(12) United States Patent
Wagner et al.

(10) Patent No.: US 10,940,427 B2
(45) Date of Patent: *Mar. 9, 2021

(54) PROCESS FOR ADSORBER REGENERATION

(71) Applicant: BASF SE, Ludwigshafen (DE)

(72) Inventors: Hans-Guenter Wagner, Neuleiningen (DE); Christoph Bayer, Nuremberg (DE); Lothar Karrer, Pfungstadt (DE); Heinz Ruetter, Xanten (DE); Patrik Pietz, Shanghai (CN); Sven Crone, Limburgerhof (DE); Markus Eggersmann, Speyer (DE); Kam Wing Wong, Tsuen Wan (CN)

(73) Assignee: BASF SE

( * ) Notice: Subject to any disclaimer, the term of this patent is extended or adjusted under 35 U.S.C. 154(b) by 0 days.

This patent is subject to a terminal disclaimer.

(21) Appl. No.: 15/517,848

(22) PCT Filed: Oct. 9, 2014

(86) PCT No.: PCT/CN2014/088232
§ 371 (c)(1),
(2) Date: Apr. 7, 2017

(87) PCT Pub. No.: WO2016/054789
PCT Pub. Date: Apr. 14, 2016

(65) Prior Publication Data
US 2017/0246585 A1      Aug. 31, 2017

(51) Int. Cl.
*B01D 53/04* (2006.01)
*B01J 20/08* (2006.01)
(Continued)

(52) U.S. Cl.
CPC .......... *B01D 53/0423* (2013.01); *B01J 20/08* (2013.01); *B01J 20/3408* (2013.01);
(Continued)

(58) Field of Classification Search
CPC .................. C07C 7/12; B01D 2259/4009
(Continued)

(56) References Cited

U.S. PATENT DOCUMENTS

| 3,208,157 A | 9/1965 | Stark |
| 4,814,517 A * | 3/1989 | Trubac .................... C07C 41/36 568/697 |

(Continued)

FOREIGN PATENT DOCUMENTS

| CN | 103254932 A | 8/2013 |
| DE | 10 2008 007 081 A1 | 8/2009 |

(Continued)

OTHER PUBLICATIONS

U.S. Appl. No. 15/517,558, filed Apr. 7, 2017, Hans-Guenter Wagner, et al.

(Continued)

*Primary Examiner* — Youngsul Jeong
(74) *Attorney, Agent, or Firm* — Faegre Drinker Biddle & Reath LLP

(57) ABSTRACT

Disclosed is a process for the regeneration of an adsorber. For the regeneration a liquid stream (S2) is applied which is obtained by hydrogenation of a stream (S1) comprising at least one alkane and least one olefin. The stream (S2) comprises one alkane and a reduced amount of at least one olefin compared to the amount in the stream (S1). Then the stream (S2) is converted from the liquid into the gaseous phase and the adsorber is regenerated by contact with the gaseous stream (S2).

20 Claims, 2 Drawing Sheets

Figure 1:
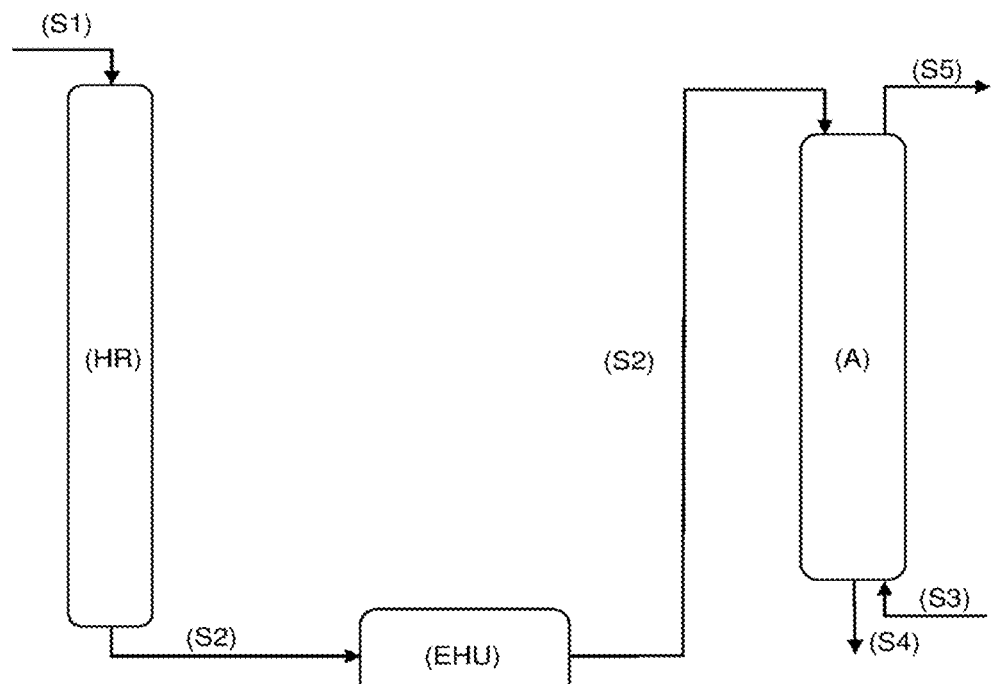

(51) Int. Cl.
  *C07C 2/06* (2006.01)
  *C07C 7/12* (2006.01)
  *C10G 25/12* (2006.01)
  *C10G 67/06* (2006.01)
  *B01J 20/34* (2006.01)

(52) U.S. Cl.
  CPC ....... *B01J 20/3433* (2013.01); *B01J 20/3458* (2013.01); *C07C 2/06* (2013.01); *C07C 7/12* (2013.01); *C10G 25/12* (2013.01); *C10G 67/06* (2013.01); *B01D 2253/104* (2013.01); *B01D 2256/24* (2013.01); *B01D 2257/556* (2013.01); *B01D 2257/70* (2013.01); *B01D 2259/4009* (2013.01); *B01D 2259/40088* (2013.01); *C10G 2300/4093* (2013.01); *C10G 2300/70* (2013.01); *C10G 2300/708* (2013.01)

(58) Field of Classification Search
  USPC ........... 585/510, 800, 250, 820, 826; 502/34
  See application file for complete search history.

(56) References Cited

U.S. PATENT DOCUMENTS

| | | | |
|---|---|---|---|
| 4,935,399 A | 6/1990 | Blackburn et al. | |
| 4,935,400 A | 6/1990 | Blackburn et al. | |
| 4,952,746 A | 8/1990 | Johnson et al. | |
| 5,177,298 A | 1/1993 | Yon et al. | |
| 6,673,239 B2 | 1/2004 | Johnson et al. | |
| 8,349,037 B2 | 1/2013 | Steiner et al. | |
| 9,943,828 B2 * | 4/2018 | Wagner | B01J 20/3408 |
| 2002/0147377 A1 * | 10/2002 | Kanazirev | B01J 20/041 585/820 |
| 2005/0075528 A1 | 4/2005 | Burkhardt et al. | |
| 2007/0123743 A1 | 5/2007 | Ng et al. | |
| 2008/0200745 A1 | 8/2008 | Sigl et al. | |
| 2011/0021851 A1 | 1/2011 | Towler et al. | |
| 2011/0200507 A1 | 8/2011 | Steiner et al. | |
| 2011/0301398 A1 | 12/2011 | Heidemann et al. | |
| 2012/0024324 A1 | 2/2012 | Force et al. | |
| 2012/0136186 A1 * | 5/2012 | Lueken | C07C 7/10 585/250 |

FOREIGN PATENT DOCUMENTS

| | | |
|---|---|---|
| EP | 0 229 994 A1 | 7/1987 |
| WO | WO 00/20359 A1 | 4/2000 |
| WO | WO 01/83407 A1 | 11/2001 |
| WO | WO 2005/056503 A1 | 6/2005 |
| WO | WO 2006/089956 A2 | 8/2006 |
| WO | WO 2010/023249 A1 | 3/2010 |
| WO | WO 2010/057905 A1 | 5/2010 |

OTHER PUBLICATIONS

U.S. Appl. No. 15/517,682, filed Apr. 7, 2017, Hans-Guenter Wagner, et al.
U.S. Appl. No. 15/517,857, filed Apr. 7, 2017, Hans-Guenter Wagner, et al.
U.S. Appl. No. 15/517,695, filed Apr. 7, 2017, Hans-Guenter Wagner, et al.
U.S. Appl. No. 15/517,286, filed Apr. 6, 2017, Hans-Guenter Wagner.
International Search Report dated May 29, 2015 in PCT/CN2014/088232.
International Preliminary Report on Patentability and Written Opinion dated Apr. 11, 2017 in PCT/CN2014/088232.
Extended European Search Report dated May 22, 2018 in Patent Application No. 14903558.6, 3 pages.

* cited by examiner

PROCESS FOR ADSORBER REGENERATION

This application is a National Stage of PCT/CN2014/088232, which was filed on Oct. 9, 2014.

The invention relates to a process for the regeneration of an adsorber. For the regeneration a liquid stream (S2) is applied which is obtained by hydrogenation of a stream (S1) comprising at least one alkane and least one olefin. The stream (S2) comprises one alkane and a reduced amount of at least one olefin compared to the amount in the stream (S1). Then the stream (S2) is converted from the liquid into the gaseous phase and the adsorber is regenerated by contact with the gaseous stream (S2).

Technical organic compositions often need to be purified from compounds containing heteroatoms in particular heteroatoms like sulfur or oxygen before use as starting materials in catalyzed reactions. These impurities may inhibit or lower the activities of catalysts. The purification can be performed by employing adsorbers.

WO 2010/057905 A1 discloses a process for the oligomerization of olefins by bringing at least one C2 to C8 olefin into contact with a nickel containing heterogeneous catalyst. Preferably the olefins are passed over an adsorption material before being brought in contact with the catalyst in order to prevent catalyst poisoning. However, WO 2010/057905 A1 does not disclose a process for the regeneration of adsorbers DE 10 2008 007 081 A1 discloses a process for the production of n-butene oligomers and 1-butene from a technical mixture-I of $C_4$-hydrocarbons. Analogously to WO 2010/057905 A1, the document mentions the need for the removal of certain compounds containing heteroatoms out of the hydrocarbon mixture intended to be used in the catalyzed oligomerization process. The document does not disclose a process for the regeneration of adsorbers.

WO 2005/056503 discloses a composite catalyst for the selective oligomerization of lower alkenes and the production of high octane products. While the oligomerization of lower alkenes and mixtures of alkenes is reported in detail, the use of adsorbers for purification of the starting materials or the regeneration of adsorbers is not mentioned. WO 01/83407 describes a process for the oligomerization of alkenes having from 3 to 6 carbon atoms using a catalyst containing a zeolite of the MFS structure type under conditions to obtain a selectively oligomeric product containing a predominant amount of certain oligomers. Like in the previously discussed document of prior art neither the use of adsorbers for purification of starting materials nor their regeneration is part of the disclosure.

In order to remove the adsorbed compounds containing heteroatoms the regeneration of the adsorbers is required periodically. This can be achieved, for example, by purging the adsorber with inert gases or hydrocarbons at elevated temperatures. Suitable regeneration media need to be essentially free of olefins and compounds containing heteroatoms, in particular free of compounds containing oxygen and sulfur. Residual olefins tend to form detrimental coke and polymer precipitates on the adsorbent, at the temperatures applied, during the regeneration process.

Technical organic compositions comprising olefins purified in an adsorber often comprise significant amounts of saturated hydrocarbons. These purified saturated hydrocarbons may be separated from the olefins in downstream process steps and would be applicable for the regeneration of the adsorbers. However, even after distillation of the product stream, the saturated hydrocarbon fraction usually still contains considerable amounts of residual olefins. Streams containing considerable amounts of olefins cannot successfully be employed for adsorber regeneration due to the increased formation of precipitates and/or coke on the adsorber surface.

U.S. Pat. Nos. 4,935,399 and 4,935,400 both describe a similar process for the reduction of hydrocarbon losses during regeneration of adsorbers containing molecular sieves for the removal of sulfur compounds from liquid hydrocarbon streams. While the process according to U.S. Pat. No. 4,935,399 comprises heating of the adsorber bed directly by a device located within the adsorber bed, in U.S. Pat. No. 4,935,400 the adsorber bed is heated by purging with gaseous hydrocarbon only. Both documents explain the use of hydrocarbon streams for the regeneration of adsorber beds containing molecular sieves, but none of them deals with the application of hydrocarbons comprising residual olefins as regeneration media.

U.S. Pat. No. 5,177,298 discloses a process for regeneration of oxygenate-containing adsorbents using hydrocarbon regenerant streams. The streams used require extra pretreatment by additional adsorbers in order to remove compounds containing sulfur or oxygen. Furthermore, U.S. Pat. No. 5,177,298 does not disclose a technical solution for the use of hydrocarbons comprising residual olefins as regeneration media.

U.S. Pat. No. 6,673,239 B2 discloses a system and process for removing water and compounds containing heteroatoms from hydrocarbons and a system and process for regeneration of adsorbents used therein. The regeneration comprises passing an isoparaffin over a water-adsorbent, then passing the isoparaffin over the heteroatom-containing compound adsorbent. However, U.S. Pat. No. 6,673,239 B2, does not deal with isoparaffins comprising residual olefins. It also provides no solution for the prevention of coking and the formation of polymers at the elevated temperatures of a regeneration process caused by residual olefins in the regeneration media.

US 2012/0024324 A1 discloses a process for regeneration of purification beds with a jet compressor in an open loop cycle. A fluid composition comprising an inert gas and a regeneration composition is used as regeneration media. Apart from hydrogen as possible secondary component, further constituents of the fluid composition are not defined. In particular the application of hydrocarbons as regeneration media is not considered in the disclosure.

The problem underlying the present invention consists in the development of a new process for regeneration of adsorbers.

The object is achieved by a process for regeneration of an adsorber comprising the following steps a) to c):

a) hydrogenation of a stream (S1) comprising at least one alkane and at least one olefin to obtain a liquid stream (S2) comprising at least one alkane and a reduced amount of at least one olefin compared to the amount in the stream (S1), b) converting the stream (S2) from liquid phase into gaseous phase and c) regenerating the adsorber by contact with the gaseous stream (S2) obtained in step b).

The process according to the present invention allows the application of hydrocarbon mixtures comprising olefins for adsorber regeneration, without significant formation of detrimental precipitates of coke and polymers on the adsorbent. Within the context of the present invention, the stream (S2) is being employed as regeneration stream or regeneration media of an adsorber.

In one embodiment of the present invention, the stream (S1) originates from an earlier process step. By consequence, the present invention allows the employment of components as regeneration media for an adsorber whereby said components have been purified earlier on the same adsorber, but which are in fact by-products, for example, within a process for producing octene by dimerization of butene. Such by-products are usually discharged as waste, but within the process of the present invention they can be successfully employed/converted into a regeneration stream.

Compared to other processes of the prior art, no additional purification step to remove compounds containing sulfur and/or oxygen and/or other heteroatoms is required since these hydrocarbon mixtures are obtained for example as side products during purification of technical organic compositions comprising olefins by means of adsorbers. The purchase of alternative regeneration media like inert gases is therefore avoided.

Furthermore, another advantage of the present invention can be seen in the fact that one embodiment of the invention allows the operation of at least one adsorber in regeneration mode parallel to the operation of at least one other adsorber in operation mode in the same plant.

It is also an advantage that according to another embodiment of the invention it is possible to collect and to recycle residual organic composition, which remained in the pores of the adsorber after finishing the operation mode, to further reduce losses of valuable organic intermediate.

In order to enrich the regeneration medium as much as possible with the adsorbed compounds containing heteroatoms and consequently consuming regeneration media in an amount as low as possible, the flow of the regeneration media can be directed, opposite to the flow of any organic composition in the operation mode of the adsorber.

For cooling of the adsorber the regeneration media can be passed through the adsorber according to the direction of the flow of any organic composition during the operation mode taking full advantage of the temperature gradient within the adsorber, further lowering the consumption of regeneration media.

In summary, operating costs and environmental burden are lowered by reduction of energy, waste and product loss due to a combination of advantageous measures implemented in the present invention. Furthermore, the present invention provides a method for efficient regeneration of adsorbers.

The invention is specified in more detail as follows:

The present invention relates to a process for the regeneration of an adsorber comprising the steps a) to c).

Within the context of the present invention, the term "adsorber" comprises the adsorbent as well as the device in which the adsorbent is embedded in. Instead of the term "adsorbent" the expression "adsorber material" may be used. The term adsorber may be used equivalently for adsorbent, even if a certain statement actually refers only to the adsorbent but not to the device in which the adsorbent is embedded in.

The adsorber can be employed for the adsorption of compounds containing oxygen and/or sulfur out of organic compositions. Preferably, the adsorber can be employed for the adsorption of ethers, alcohols, thiols, thioethers, sulfoxides, ketones, aldehydes or mixtures thereof.

Any adsorbent known to the person skilled in the art being appropriate for performing the adsorption of compounds containing oxygen and/or sulphur out of organic compositions may be applied.

Preferred adsorbents are, for example, molecular sieves with a pore diameter of 4 to 15 Å. Further, molecular sieves applicable are crystalline, natural aluminia silicates, like layer lattice silicates or synthetic molecular sieves. Furthermore, commercially available molecular sieves as sold by the Bayer AG, Dow, Union Carbide, Laporte or Mobil may be used. These molecular sieves can be, for example, zeolites of the A-, X- and Y-type. Moreover, synthetic molecular sieves comprise silicon and aluminium as main components, other atoms as side-components such as lanthanides like gallium, indium and lanthanum or other elements like nickel, cobalt, copper, zinc or silver may be useful. These can be introduced into the zeolite for example by means of an ion-exchange with exchangeable cations.

Likewise, synthetic zeolites can be employed, in which other atoms like boron or phosphorus are incorporated in the layer by co-precipitation.

Further suitable adsorbents are aluminium phosphate, silicon dioxide, kieselgur, titanium dioxide, zirconium dioxide, polymeric adsorbents and mixtures thereof.

The most preferred adsorbent is aluminium oxide, commercially available for example as Selexsorb CDL from BASF.

In one embodiment of the process according to the present invention, wherein the adsorbent in the adsorber is based on aluminium oxide and/or the adsorber can be employed for the adsorption of compounds containing oxygen and/or sulphur out of organic compositions, preferably the adsorber can be employed for the adsorption of ethers, alcohols or mixtures thereof.

The assembly, wherein the adsorber is integrated, may comprise at least one further adsorber identical to the first adsorber in respect of the adsorbent and its operation mode.

In a further embodiment of the invention, wherein the adsorber to be regenerated in step c) (step c) is defined below) is part of an assembly which contains at least one further adsorber, preferably the at least one further adsorber is under its operation mode during the regeneration of the first adsorber, and/or each adsorber within this assembly is identical in respect of the adsorbent and its operation mode.

Regeneration, in the context of the present invention, means desorption and removal of adsorbed compounds containing oxygen and/or sulfur from the adsorber, in particular from the adsorbent in the adsorber. The inventive process for regeneration of the adsorber may also comprise additional measures/steps necessary, for example, for preparation of the regeneration medium, the adsorber itself for regeneration or for enabling the adsorber after finished regeneration to be operated again for adsorption of compounds containing oxygen and/or sulphur out of organic compositions.

An adsorber, within the context of the present invention, is in operation mode, when a stream comprising an organic composition, comprising at least one alkane and/or at least one olefin and compounds containing oxygen and/or sulfur is fed into the adsorber and compounds containing oxygen and/or sulfur are adsorbed completely or at least partially from this stream on the adsorbent. The respective composition is preferably not being routed through the adsorber before.

Preferably at least 50%, more preferably at least 80%, most preferably at least 97% of the compounds containing oxygen and/or sulfur are adsorbed from the stream during the operation mode of the respective adsorber according to the preceding paragraph.

An adsorber, within the context of this invention, is in regeneration mode when measures to remove or measures related to the removal of adsorbed compounds containing oxygen and/or sulphur from the adsorbent are carried out or optionally the definition of the operation mode does not apply.

Consequently, the adsorber of the present invention can be operated either in operation mode or in regeneration mode.

The steps a), b) and c) within the process for regeneration of an adsorber according to the present invention are defined as follows:

In step a) a stream (S1) is hydrogenated comprising at least one alkane and at least one olefin to obtain a liquid stream (S2) comprising at least one alkane and a reduced amount of at least one olefin compared to the amount in the stream (S1).

Preferably, the amount of the at least one olefin in stream (S1) is, reduced due to the hydrogenation by at least 70%, more preferably by at least 90% and most preferably by at least 95% compared to the respective amount in stream (S1) before performing step a) in order to obtain the stream (S2).

Usually, all olefins, independent of their numbers of olefinic double bonds, are hydrogenated by the hydrogenation conditions and consequently their amount is reduced. It is possible that olefins containing more than one olefinic double bond are only partially hydrogenated and one or more of the olefinic double bonds per molecule in at least a part of these molecules is left unsaturated after performing step a).

Stream (S1) and/or stream (S2) may comprise at least one linear, branched and/or cyclic alkane. Preferably the alkane contains 1 to 14, more preferably 3 to 10, most preferably 4 to 6 carbon atoms in its longest chain.

The at least one alkane can be, for example, selected from the group: methane, ethane, propane, butane, pentane, hexane, heptane, octane, nonane and decane. Preferably the at least one alkane is butane.

In the context of the present invention, if not stated otherwise, it is not differentiated between the different isomers of a certain alkane. For example, the term butane may refer to n-butane and/or isobutane.

The stream (S1) and/or stream (S2) may comprise in a specific embodiment one or more further alkanes different from butane, which may be selected from the same alkanes as specified above.

The at least one olefin in stream (S1) and/or stream (S2) may comprise a linear, branched, cyclic monoolefin and/or a linear, branched, cyclic olefin containing more than one olefinic double bond. Preferably the olefin has 2 to 14, more preferably 3 to 10, most preferably 4 to 6 carbon atoms in its longest carbon chain.

If more than one stereoisomer of an olefin exists, e.g. the corresponding cis- and trans-isomer, these isomers are, in the context of the present invention, regarded as equivalent. Further, it is not differentiated between constitutional isomers of monoolefins. For example the term butene may comprise the constitutional isomers 1-butene, cis-2-butene and/or trans-2-.

Monoolefins can be, for example, selected from the group: ethene, propene, butene pentene, hexene, heptene, octene, nonene and decene. Preferably, the olefin is butene. If at least one olefin containing more than one olefinic double bond is present, this olefin is preferably a diene, more preferably butadiene.

The stream (S1) and/or stream (S2) may comprise in a specific embodiment one or more further olefins different from butene which may be selected from the same olefins as specified above.

In step a), the stream (S1) can comprise at least one alkane and at least one olefin in a total of at least 99 wt.-%, more preferably in a total of at least 99.5 wt.-%, most preferably in a total of at least 99.9 wt.-%.

The stream (S1) may comprise butane and butene, preferably at least 96 wt.-% butane and not more than 4 wt.-% butene.

Preferably, the stream (S2) comprises not more than 1000 wt.-ppm olefin, preferably not more than 500 wt.-ppm olefin, most preferably not more than 100 wt.-ppm olefin, wherein the olefin is preferably butene.

Further, the stream (S2) can comprise at least 99 wt.-% of at least one alkane, preferably at least 99.5 wt.-% of at least one alkane, most preferably at last 99.9 wt.-% of at least one alkane, wherein the alkane is preferably butane.

Preferably, the amount of olefins containing more than one olefinic double bond in stream (S1) and/or stream (S2) is lower than 500 ppm, more preferably lower than 300 ppm, most preferably lower than 100 ppm, preferably the olefin containing more than one olefinic double bond is a diene, wherein the olefin is preferably butadiene.

The hydrogenation may be carried out by any appropriate method known to the person skilled in the art.

The hydrogenation may be a catalyzed hydrogenation using at least a catalyst and a hydrogen source.

Preferably, the catalyst comprises d-block elements, more preferably, for example, Pd, Pt, Ru, Ir, Rh, Cu, Ni or Co, most preferably Pd, Ni, Pt or Rh, in particular preferably Pd or Ni.

The hydrogenation can be performed using $H_2$-gas and/or catalytic transfer hydrogenation, employing for example ammonium formate, silyl hydrides, $NaBH_4$, cyclohexene or alcohols like methanol and propanol as hydrogen source. Preferably, the hydrogenation is carried out using $H_2$-gas as hydrogen source.

The hydrogen source and the solvent may be identical, for example, in the case of alcohols like methanol.

Any solvent known to the person skilled in the art being appropriate for performing the hydrogenation may be employed.

In general polar-protic, polar-nonprotic and/or unpolar solvents can be employed, for example methanol, ethanol, propanol, isopropanol, tetrahydrofuran or toluene.

Alternatively, the hydrogenation can be carried out without using any solvent.

In a preferred embodiment, the hydrogenation is carried out without the use of any solvent and with $H_2$-gas as hydrogen source.

Any reactor known to the person skilled in the art being appropriate for performing the hydrogenation may be employed.

Preferably a trickle bed reactor is employed for performing the hydrogenation.

In one embodiment of the invention the stream (S1) originates from an organic composition which has been earlier purified by the same adsorber or by a similar further adsorber during the operation mode of the respective adsorber.

This embodiment may also include an oligomerization of olefins, preferably a dimerization of butene to octene, and/or a distillation step to separate butane from butene may be carried out prior to step a) followed by a purification of an organic composition using at least one adsorber in an operation mode.

The pressure of stream (S2) in step a) may be of 5 to 80 bar, more preferably of 10 to 50 bar, most preferably of 20 to 30 bar.

In one embodiment of the process, in step a),
i) the stream (S1) comprises butane and butene, preferably at least 96 wt.-% butane and not more than 4 wt.-% butene, and/or
ii) the stream (S2) comprises not more than 1000 wt.-ppm olefin, preferably not more than 500 wt.-ppm olefin, most preferably not more than 100 wt.-ppm olefin, wherein the olefin is preferably butene, and/or
iii) the stream (S2) comprises at least 99 wt.-% of at least one alkane, preferably at least 99.5 wt.-% of at least one alkane, most preferably at least 99.9 wt.-% of at least one alkane, wherein the alkane is preferably butane.

In step b) the stream (S2) is converted from liquid phase into gaseous phase.

The conversion may be carried out by any appropriate method or apparatus known to the person skilled in the art.

The conversion in step b) may be carried out by lowering the pressure and/or heating of the liquid stream (S2), preferably by employing at least one evaporator and/or at least one super-heater and/or at least one flash vessel.

In a preferred embodiment, liquid stream (S2), originating from step a), with a pressure of 5 to 80 bar, preferably of 10 to 50 bar, most preferably of 20 to 30 bar is, for the conversion according step b), fed into a flash vessel, wherein the pressure of liquid stream (S2) is lowered to 4 to 16 bar, preferably to 7 to 13 bar, most preferably to 8 to 11 bar.

Lowering the pressure of liquid stream (S2), preferably in a flash vessel, compared to the pressure of liquid (S2) obtained in step a), can result in conversion of at least a part of liquid stream (S2) into gaseous phase. Remaining liquid stream (S2) at lowered pressure may be converted into gaseous phase by use of at least one evaporator.

By lowering the pressure of liquid stream (S2), preferably in a flash vessel, compared to the pressure of liquid stream (S2) obtained in step a), 0 to 80%, preferably less than 10% of liquid stream (S2) may be converted into gaseous phase.

Alternatively, the liquid stream (S2) may be converted into a gaseous phase, preferably with at least one evaporator, with or without prior lowering the pressure compared to the pressure obtained for the stream (S2) in step a).

Within the present invention, an evaporator is a device which converts a liquid stream into gaseous phase by transfer of heat to the liquid stream.

It is also possible to use two or more evaporators which are passed by stream (S2) in series and/or in parallel.

Any evaporator known to the person skilled in the art being appropriate for performing the evaporation may be applied.

Examples of evaporators are electric evaporators and evaporators transferring heat by means of a heat transfer medium, like steam (gaseous water) or other gaseous media, hydrocarbons, oils or salts. Preferably, the evaporators are of the Kettle type.

The conversion of liquid stream (S2) into gaseous phase according to step b) may also comprise super-heating.

Super-heating, in the context of the present invention, means further increasing the temperature of the already gaseous stream (S2), preferably by transfer of heat to the gaseous stream (S2).

Any super-heater known to the person skilled in the art being appropriate for the super-heating may be applied.

Super-heating may be performed with one or more super-heaters. When more than one super-heater is used, the super-heaters can be arranged in series and/or in parallel.

Examples of possible super-heaters are electric super-heaters and super-heaters transferring heat by means of a heat transfer medium, suitable gaseous media, hydrocarbons, oils or salts. Preferably, super-heaters are of the shell-and-tube-type.

Evaporating and super-heating may be performed in different devices and/or be combined in at least one device capable to fulfill both functions, for instance a shell-and-tube heat exchanger stacked on top of a Kettle-type evaporator.

When evaporators and/or super-heaters based on a heat transfer medium are used, the same stream of heat transfer medium may be passed through only one evaporator or super-heater or through more than one evaporator or super-heater. The same stream of heat transfer medium can be used for evaporators or super-heaters or for evaporators and super-heaters.

The same type of heat transfer medium can be applied for all evaporators and/or super-heaters or different types of heat transfer media for each individual device or a group of evaporators and/or super-heaters may be used.

Depending on the temperature actually required at a given time of the process, the heat transfer to the liquid or gaseous stream (S2) by the respective evaporators and/or super-heaters may be reduced, stopped completely and/or one or any number of evaporators and/or one or any number of super-heaters may be by-passed by stream (S2).

Preferably gaseous stream (S2) is passed through all evaporators and/or super-heaters and heat transfer is reduced or stopped when lower temperatures for gaseous stream (S2) are required.

Preferably evaporators and/or super-heaters are by-passed if liquid stream (S2) is required.

In step c) the adsorber is regenerated by contact with the gaseous stream (S2) obtained in step b).

In step c) the regeneration of the adsorber can be carried out at a temperature in the range of 230 to 270° C., preferably at 250° C. and/or by passing the gaseous stream (S2) through a device containing the adsorber.

The pressure of gaseous stream (S2) in step c) is usually identical to the pressure of gaseous stream (S2) as obtained in step b) or a) or lower.

Preferably, the heating rate of the adsorber does not exceed 60° C./h, more preferably it does not exceed 40° C./h.

Step c) of the inventive process may comprise one or more of the following component steps c1) to c5):
c1) heating the adsorber by contact with the gaseous stream (S2), wherein the gaseous stream (S2) is condensed within the adsorber,
c2) heating the adsorber by contact with the gaseous stream (S2) up to a temperature in the range of 230 to 270° C., preferably 250° C., without any condensation of the gaseous stream (S2) within the adsorber,
c3) regeneration of the adsorber at a temperature in the range of 230 to 270° C., preferably 250° C. by contact with the gaseous stream (S2),
c4) cooling of the adsorber by contact with the gaseous stream (S2) to a temperature in the range of 80-120° C.,
c5) cooling of the adsorber by contact with the liquid stream (S2) obtained in step a) to a temperature below 80° C., preferably to a temperature in the range of 40 to 60° C.

Preferably, step d) (as defined below) is carried out prior to step c) and step c) comprises the component steps c1), followed by c2), followed by c3), followed by c4) and followed by c5).

Condensation, meaning conversion from gaseous into liquid phase, of the components comprised in stream (S2) in the step c), in particular in the step c1), usually takes place if at least one position, meaning a spacial element, inside the adsorber, being the adsorbent and/or the adsorber wall, has a temperature, which is below the dew point temperature of the respective components contained in the gaseous stream (S2), present at that the position.

In one embodiment of the invention, the condensate obtained in step c1) contains the stream (S2) and the residue of the organic composition which was not removed from the adsorber when carrying out draining step d), and the condensate is optionally collected in a device, preferably in a buffer vessel, in order to pass the collected condensate through an adsorber during its operation mode.

The temperature of the gaseous stream (S2) is preferably not more than 100° C., more preferably not more than 60° C., higher than the temperature of the adsorber, especially during the heating steps c1) and/or c2).

The temperature of the gaseous or optionally liquid stream (S2) is preferably not more than 100° C., more preferably not more than 60° C., lower than the temperature of the adsorber, especially during the cooling steps c4) and/or c5).

In one embodiment of the invention, the temperature of the gaseous or optionally liquid stream (S2) is not more than 100° C., preferably not more than 60° C., lower than the adsorber, especially during the cooling steps c4) and/or c5).

In a further embodiment of the invention:
i) the heating rate of the adsorber does not exceed 60° C./h, preferably it does not exceed 40° C./h and/or
ii) the temperature of the gaseous stream (S2) is not more than 100° C., preferably not more than 60° C., higher than the temperature of the adsorber, especially during the heating steps c1) and/or c2), and/or
iii) the temperature of the gaseous or optionally liquid stream (S2) is not more than 100° C., preferably not more than 60° C., lower than the temperature of the adsorber, especially during the cooling steps c4) and/or c5).

In the context of the invention, it is of advantage, if the flow direction of the gaseous stream (S2) through the adsorber in steps c1), c2) and/or c3) is opposite to the flow direction of any organic composition through the same adsorber during its operation mode, and/or the gaseous stream (S2) in step c4) and/or the liquid stream (S2) in step c5) have the same flow direction through the adsorber as the flow direction of any organic composition through the same adsorber during its operation mode.

Subsequent to step c), the outflow obtained from the adsorber, comprising gaseous stream (S2) and optionally impurities removed from the adsorber, can be condensed, preferably by employing at least one condenser and/or at least one cooler.

Any condenser known to the person skilled in the art being appropriate for performing the coolers and/or condensors may be employed.

Condensing can be performed using one condenser and/or cooler or two or more cooler and/or condenser connected in series and/or in parallel.

After finishing the regeneration of the adsorber according to step c), the adsorber can be switched into its operation mode by feeding it with an organic composition to be purified.

In one embodiment of the invention:
i) subsequent to step c), the outflow obtained from the absorber, comprising gaseous stream (S2) and the impurities removed from the adsorber, is condensed, preferably by employing at least one condenser and/or at least one cooler and/or ii) after finishing the regeneration of the adsorber according to step c), the adsorber is switched into its operation mode by feeding it with an organic composition to be purified.

Besides the steps a), b), c) in a further embodiment the invention may comprise a further draining step d), carried our prior to step c), in order to at least partially remove an organic composition which was passed through the adsorber during its operation mode.

Preferably at least 10%, more preferably at least 30%, most preferably at least 40%, in particular preferably at least 60% of the organic composition may be removed from the adsorber in the draining step d).

The drained organic composition may be collected in order to reduce losses of valuable organic composition to be purified during operation mode.

In a preferred embodiment of the invention, the process for the regeneration of an adsorber comprises the following steps a) to c):
a) hydrogenation of a stream (S1) comprising at least butane and at least butene to obtain a liquid stream (S2) comprising at least butane and a reduced amount of butene compared to the amount in the stream (S1),
b) converting the stream (S2) from liquid phase into gaseous phase and
c) regenerating the adsorber by contact with the gaseous stream (S2) obtained in step b)
and wherein the stream (S1) comprises at least 96 wt.-% butane and not more than 4 wt.-% butene as well as the stream (S2) comprises not more than 1000 wt.-ppm of olefin.

FIGURES

The FIGS. 1 to 4 illustrate certain aspects of the invention. For the sake of clarity not all applicable components and embodiments are drawn in one and/or all figures. Embodiments shown in different figures may be combined with each other and do not exclude the incorporation of further components within the limits of the disclosure of the specification.

Figure 2:
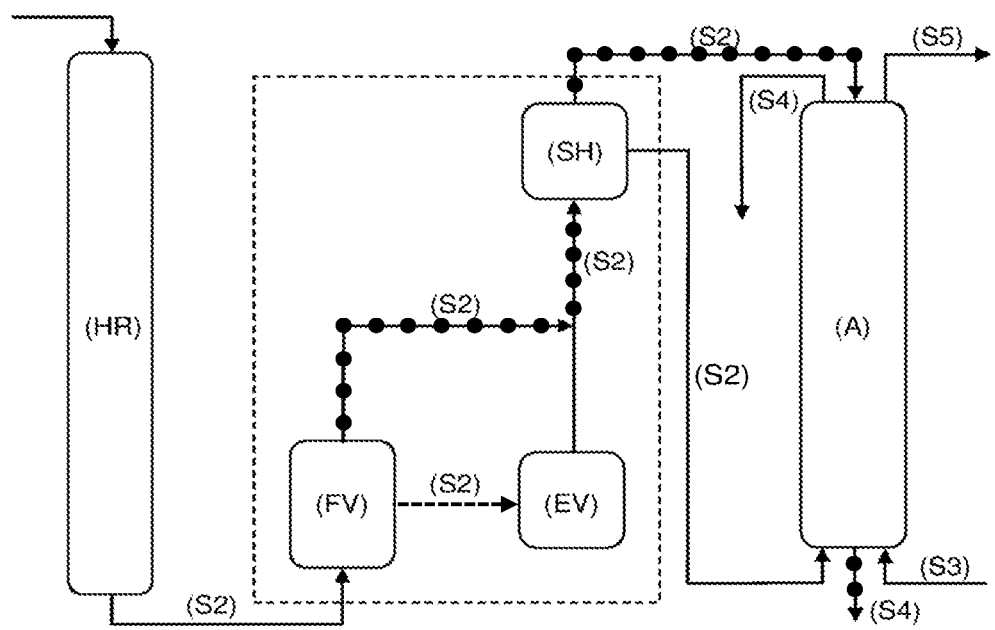

FIG. 1 illustrates the most basic assembly of the present invention. According to step a) of the process of the present invention a stream (S1) is fed into the hydrogenation reactor (HR). The stream (S1) is converted in the hydrogenation reactor (HR) into the stream (S2) and routed through the evaporation/heating unit (EHU) in order to be converted from the liquid into the gaseous phase. Then the adsorber (A) is regenerated by contact with gaseous stream (S2) coming from the evaporation/heating unit (EHU). The stream (S4) is leaving adsorber (A) during regeneration mode but not during operation mode of the adsorber (A). The stream (S4) comprises at least the stream (S2) and/or compounds containing oxygen and/or sulphur and/or optionally some residue of organic composition. The streams (S3) and (S5) are only present during operation mode. The stream (S3) comprises organic composition and compounds containing oxygen and/or sulphur. The stream (S5) comprises organic composition and no compounds containing oxygen and/or sulphur or a lower amount of compounds containing oxygen and/or sulphur than stream (S3). Stream (S5) is leaving adsorber (A) on the opposite end of adsorber (A), chosen for the introduction of stream (S3) into the adsorber (A). In other words, stream (S4) usually additionally comprises (compared to stream (S2)) those elements (such as compounds containing oxygen and/or sulphur) which were adsorbed by the adsorber from stream (S3) during its operation mode. FIG. 2 demonstrates one possible embodiment for the evaporation/heating unit (EHU). Liquid stream (S2) is fed into a flash vessel (FV) and routed from there directly (see dashed lines) and/or indirectly over an evaporator (EV) to a super-heater (SH). Coming from super-heater (SH) stream (S2) can be fed into adsorber (A) opposite (see dashed lines) or according to the direction of the flow of stream (S3).

Figure 3:
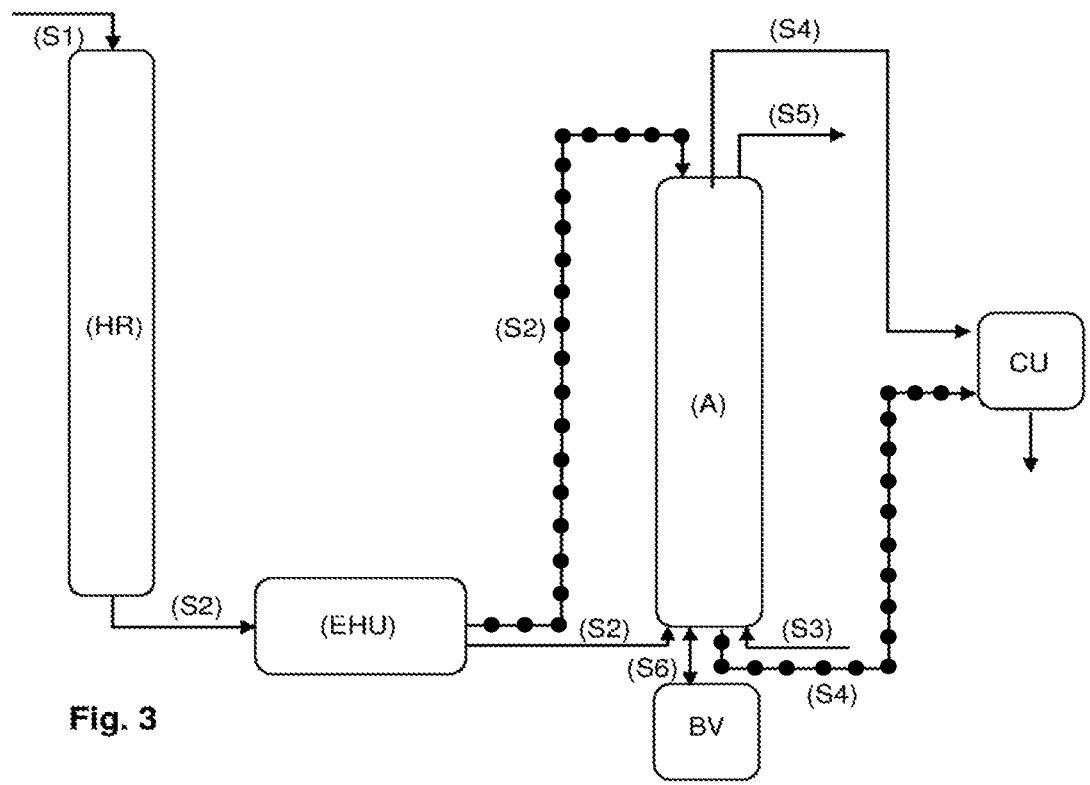

Besides the possible set-ups shown in FIG. 1 and FIG. 2, in FIG. 3 further optional components are displayed; a buffer vessel (BV), connected over stream (S6) with adsorber (A) and a cooling unit (CU) for cooling for example of the streams (S4). Stream (S6) can be routed in any direction between at least adsorber (A) and buffer vessel (BV). Stream (S6) comprises at least organic composition and/or stream (S2) and/or compounds containing oxygen and/or sulphur. Cooling unit (CU) comprises at least one cooler and/or condenser which are serially connected and/or parallel-connected with each other.

Figure 4:
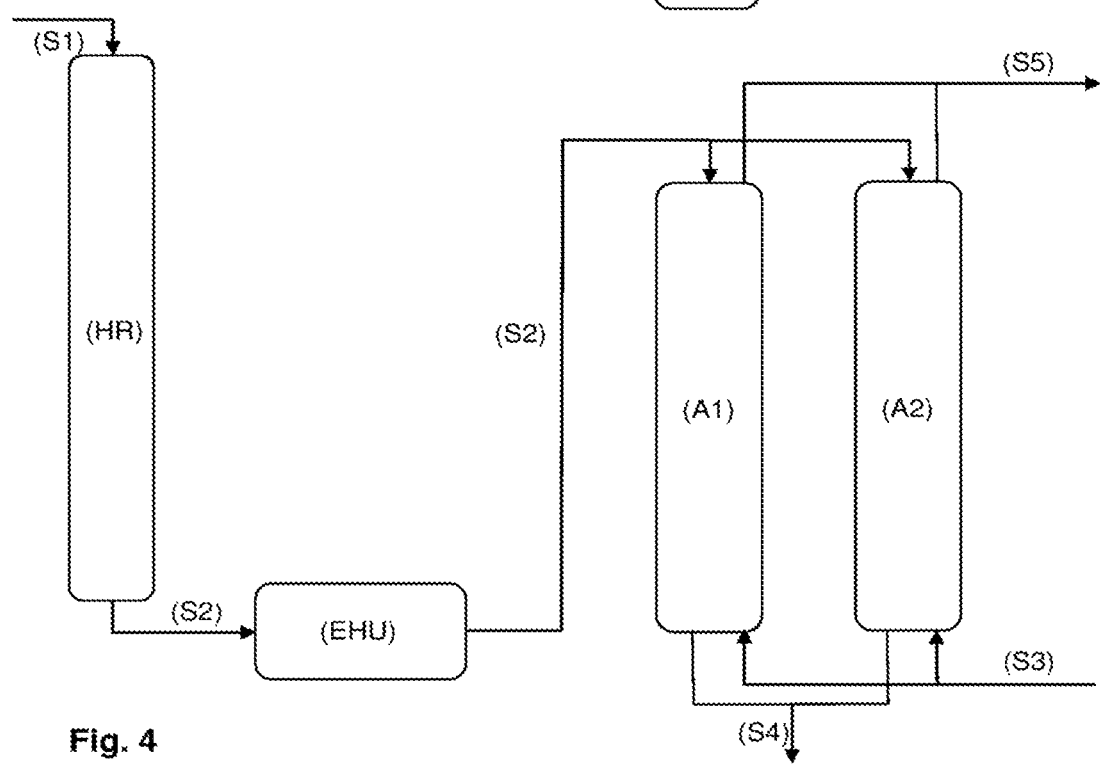

FIG. 4 shows an embodiment of the invention employing at least two adsorbers (A1) and (A2). The set-up makes it possible to run one adsorber in operation mode and the other in parallel in regeneration mode. In this case stream (S3) is fed only into the adsorber in operation mode and stream (S2) is only fed into the adsorber in regeneration mode. Consequently, stream (S4) is only leaving the adsorber in regeneration mode and stream (S5) is only leaving the adsorber in operation mode.

The invention claimed is:

1. A process for regenerating an adsorber, the process comprising:
   a) hydrogenating a stream (S1) comprising an alkane and an olefin to obtain a liquid stream (S2) comprising the alkane and a reduced amount of the olefin compared to an amount of the olefin in the stream (S1), wherein
      i) the stream (S1) comprises at least 96 wt-% of butane and not more than 4 wt-% of butene;
      ii) the amount of olefins comprising more than one olefinic double bond in the stream (S1) is lower than 500 wt-ppm;
      iii) the liquid stream (S2) comprises not more than 1000 wt-ppm of the olefin; and
      iv) the liquid stream (S2) comprises at least 99 wt-% of the butane;
   b) convening the liquid stream (S2) into a gaseous stream (S2);
   c) contacting the adsorber with the gaseous stream (S2) at a temperature in a range of from 230 to 270° C. in order to regenerate the adsorber; and
   d) subsequent to the contacting c), condensing an outflow obtained from the adsorber, wherein the outflow obtained from the adsorber comprises the gaseous stream (S2) and impurities removed from the adsorber.

2. The process of claim 1, wherein the stream (S1) comprises the alkane and the olefin in a total of at least 99 wt-%.

3. The process of claim 1, wherein the adsorber comprises an adsorbent comprising aluminum oxide, or the adsorber adsorbs compounds comprising oxygen or sulfur out of organic compositions.

4. The process of claim 3, wherein the adsorber adsorbs ethers, alcohols, thiols, thioethers, sulfoxides, ketones, aldehydes, or mixtures thereof.

5. The process of claim 1, wherein the converting b) of the liquid stream (S2) to the gaseous stream (S2) occurs by lowering the pressure of the liquid stream (S2), or by heating the liquid stream (S2).

6. The process of claim 5, wherein the converting b) of the liquid stream (S2) to the gaseous stream (S2) occurs within at least one evaporator, within at least one superheater, or within at least one flash vessel.

7. The process of claim 1, wherein the contacting c) of the adsorber with the gaseous stream (S2) occurs by passing the gaseous stream (S2) through a device comprising the adsorber.

8. The process of claim 1, wherein, prior to the contacting c), a draining step is carried out, and
   wherein an organic composition which was passed through the adsorber during its operation mode is at least partially removed.

9. The process of claim 1, wherein the contacting c) comprises:
   c1) heating the adsorber by contacting the adsorber with a first portion of the gaseous stream (S2), wherein at least a portion of the first portion of the gaseous stream (S2) is condensed within the adsorber;
   c2) heating the adsorber by contacting the adsorber with a second portion of the gaseous stream (S2) up to a temperature in a range of from 230 to 270° C. without any condensation of the second portion of the gaseous stream (S2) within the adsorber, wherein the condensed portion of step c1) is re-vaporized to a gaseous state;
   c3) regenerating the adsorber at a temperature ranging from 230 to 270° C. by contacting the adsorber with the second portion of the gaseous stream (S2);
   c4) cooling the adsorber, by contacting the adsorber with a third portion of the gaseous stream (S2) to a temperature in a range of from 80 to 120° C.; and
   c5) cooling the adsorber by contacting the adsorber with the liquid stream (S2) obtained in the hydrogenating a) to a temperature below 80° C.

10. The process of claim 9, wherein, prior to the contacting c), a draining step is carried out, and
    wherein an organic composition which was passed through the adsorber during its operation mode is at least partially removed.

11. The process of claim 10, wherein a condensate, obtained in the heating c1), comprises the liquid stream (S2) and a residue of the organic composition which was not removed from the adsorber during the draining step, and the condensate is optionally collected in a device to pass collected condensate through the adsorber during the operation mode of the adsorber.

12. The process of claim 10, wherein:
    a flow direction of the first portion of the gaseous stream (S2) during the contacting with the adsorber in the heating c1), a flow direction of the second portion of the gaseous stream (S2) during the heating c2), or the regenerating c3), is opposite to a flow direction of the organic composition passed through the adsorber during the operation mode of the adsorber; or
    the third portion of the gaseous stream (S2) in the cooling c4), or the liquid stream (S2) in the cooling c5), have the same flow direction during the contacting with the adsorber as a flow direction of the organic composition passed through the adsorber during the operation mode of the adsorber.

13. The process of claim 1, wherein:
    i) a heating rate of the adsorber does not exceed 60° C./h;
    ii) a temperature of the gaseous stream (S2) is not more than 100° C. higher than a temperature of the adsorber; or iii) a temperature of the gaseous stream (S2), or optionally a temperature of the liquid stream (S2), is not more than 100° C. lower than the temperature of the adsorber.

14. The process of claim 1, comprising:
after regeneration of the adsorber by the contacting c), subjecting the adsorber to an operation mode by feeding the adsorber with an organic composition to be purified.

15. The process of claim 1, wherein the adsorber to be regenerated in the contacting c) is part of an assembly comprising further adsorber.

16. The process of claim 15, wherein the further adsorber is subjected to an operation mode during regeneration of the adsorber, or the adsorber and the further adsorber are identical in form and operation mode.

17. The process of claim 1, wherein the stream (S1) originates from an organic composition which has been earlier purified with the adsorber or which has been earlier purified with a further adsorber during an operation mode of the respective adsorber.

18. The process of claim 1, wherein the contacting c) increases an amount of oxygen-comprising compounds in an outflow relative to an inflow.

19. The process of claim 1, wherein the contacting c) does not decrease an amount of oxygen-comprising compounds in an outflow relative to an inflow.

20. The process of claim 19, wherein the inflow is the gaseous stream (S2).

* * * * *